United States Patent [19]

Guglielmo et al.

[11] Patent Number: 4,900,872
[45] Date of Patent: Feb. 13, 1990

[54] PROCESS FOR THE PREPARATION OF FLUOROHALOGENATED ETHERS STARTING FROM FLUOROOXY-COMPOUNDS AND HALOGENATED OLEFINS

[75] Inventors: Giorgio Guglielmo, Venice; Gian P. Gamberetto, Padua, both of Italy

[73] Assignee: Ausimont S.p.A., Milan, Italy

[21] Appl. No.: 361,775

[22] Filed: May 26, 1989

Related U.S. Application Data

[63] Continuation of Ser. No. 119,170, Nov. 10, 1987, abandoned.

[30] Foreign Application Priority Data

Nov. 14, 1986 [IT] Italy ................................ 22349 A/86

[51] Int. Cl.$^4$ .............................................. C07C 41/06
[52] U.S. Cl. ..................................... 568/684; 568/614; 568/615; 568/663; 568/669; 568/677
[58] Field of Search ............... 568/614, 615, 663, 669, 568/677, 684

[56] References Cited

U.S. PATENT DOCUMENTS 4,577,044  3/1986  Campbell et al. .................. 568/684

FOREIGN PATENT DOCUMENTS 201871  11/1986  European Pat. Off. .

*Primary Examiner*—Howard T. Mars
*Attorney, Agent, or Firm*—Stevens, Davis, Miller & Mosher

[57] ABSTRACT

Improved process for the preparation of fluorohalogenated ethers by reaction of a fluorinated fluorooxycompound with a halogenated olefin, performed in liquid phase, in the presence of an inert solvent, at low temperature, the fluoroxycompound being continuously fed in form of solution in an inert solvent.

3 Claims, No Drawings

PROCESS FOR THE PREPARATION OF FLUOROHALOGENATED ETHERS STARTING FROM FLUOROOXY-COMPOUNDS AND HALOGENATED OLEFINS

This application is a continuation of application Ser. No. 119,170, filed Nov. 10, 1987, now abandoned.

The present invention relates to an improved process for obtaining fluorohalogen ethers.

The fluorohalogenated ethers prepared according to this process are in particular suitable to be halogenated to give the corresponding perfluorovinylethers.

It is known to react the fluoroxycompounds in gaseous phase, at low temperature, with halogenated olefins to obtain the fluorohalogenated ethers of the above mentioned type (see Italian Patent Application 20781 A/85).

It is well known that fluoroxy-compounds having a number of carbon atoms more than 1 are very explosive and they are very difficult to deal with.

Patent application 20781 A/85 in the name of the Patentee describes a process in which the fluoroxycompound is continuously fed in gaseous phase in order to prepare in a continuous way fluorohalogenated ethers.

The disadvantage of this process resides in the fact that the yield for fluoroxy compounds containing more than two carbon atoms are unsatisfactory.

Due to the fact that the latter fluoroxy compounds are very explosive the teaching of the prior art is very poor.

Object of the present invention is to prepare fluorohalogenated ethers in continuous way by using fluoroxy compounds having more than two carbon atoms.

Object of the present invention is an improved process for preparing fluorohalogenated ether having the general formula:

$$(R)_nC(F)_m-O-CAF-CA'F_2 \quad (1)$$

wherein A' and A' equal or different among them are selected from chlorine and bromine, R is an alkyl, cycloalkyl, aromatic, heterocyclic or polyether radical containing from 1 to 20 carbon atoms, partially or wholly halogenated with bromine, chlorine, iodine and/or fluorine, n is an integer showen between 1 and 2, m is an integer equal to 3-n, being understood that the value n=2 comprises the compounds wherein C belongs to a cyclic ring.

The process is based on the reaction between a fluoroxycompound of the general formula:

$$(R)_nC(F)_m-OF$$

with an olefin CAF=CA'F wherein the symbols R, A, A', n and m have the above specified meaning, the reaction being carried out in liquid phase, at temperature comprised between −150° and 0° C., preferably between −40° and −100° C.

The process is caracterized in that the fluoroxycompound is continuously fed into the reactor, in form of a solution in an inert solvent, at a concentration lower than 50% by weight, the mentioned solution being obtained continuously by contacting the fluoroxycompound continuously fed in gaseous form, preferably diluted with an inert gas, with the reaction inert solvent.

As inert gaseous diluent of the starting fluoroxycompounds, the same reaction solvent may be used provided that it is in gaseous form in the compositions in which the fluoroxycompound is suppplied. The halogenated olefins must be always present in the reaction phase in excess on the fluoroxycompound. The halogenated olefin may be fed all at the beginning into the reactor in liquid form, optionally diluted with an inert solvent which may be the same solvent used for the fluoroxycompound to be dissolved. Alternatively, also the olefin may be continuously fed.

Solvents suitable for the reaction are in particular chlorofluorocarbons, perfluorocarbons, and perfluoroethers or perfluoropolyethers.

In the process according to the invention, the fluoroxycompound coming directly from the reactor of the synthesis of the same, in gaseous form, can be advantageously used. In fact, the inert diluents used in the reaction for the synthesis of the fluoroxycompound starting from fluorine and acyl fluoride can be sompatible and suitable also for the present process.

Examples of perfluorohalogenated ethers which may be prepared by the process according to the invention are as follows:

$CF_3-CF_2-O-CClF-CClF_2$
$CClF_2-CF_2-O-CClF-CClF_2$
$CCl_2-F-CF_2-O-CClF-CClF_2$
$CCl_3F_2O-CClF-CClF_2$
$CBrF_2-CF_2-O-CClF-CClF_2$
$CF_3-O-CF_2-CF_2-O-CClF-CClF_2$
$C_2F_5-O-CF_2-CF_2-O-CClF-CClF_2$
$(CF_3)_2-CF-O-CClF-CClF_2$.

The following examples are given only to illustrate the possible performance of the process according to the invention.

EXAMPLE 1

A gaseous stream of fluoroxyperfluoroethane obtained by reacting trifluoroacetylfluoride and elemental fluorine fed separately into a catalytic reactor in the presence of ALGOFLON A114® (dichlorotetrafluoroethane) in the gaseous phase, contains 20% by volume of $C_2F_5OF$ and 80% of $C_2F_4Cl_2$.

This gaseous stream is cooled in a glass condenser externally cooled to −80° C. with a flow of 18.7 Nl/h and is for the most part condensed. The thus obtained solution is poured dropwise into a reactor cooled to −80° C. containing a strongly agitated solution of symmetric dichlorodifluoroethylene (230 g) in 600 g of ALGOFLON A12® ($CF_2Cl_2$).

After 10 hours the fed perfluoroxycompound is equivalent to 95% of the olefin. The feeding is interrupted and the liquid in the reactor is distilled off.

A fraction of product boiling at 58°-60° C. (356 g; yield 80%) is recovered and identified as $CF_3-CF_2-O-CFCl-CF_2Cl$ by the mass spectrometry.

EXAMPLE 2

A gaseous stream containing 20% by volume of chlorotetra fluoroxyethane $CF_2Cl-CF_2-OF$ and 80% by volume of ALGOFLON A114® obtained as in the preceding example is cooled in a condenser cooled to −30° C. wherein it condenses almost completely and the thus obtained solution is poured dropwise into a strongly agitated reactor, externally cooled to −80° C. and containing 200 g of olefinic CFCl=CFCl dissolved in 500 g of ALGOFLON A114®.

After 20 hours, always keeping the flow of the gas at 7.8 Nl/h the fed fluoroxycompound is about 92% of the olefin. At this moment the feeding is interrupted, the content of the reactor is distilled off and 79 g of a fraction boiling at 90°–95° C., is recovered the 95% of which consists of the compound $CF_2Cl-CF_2-O-CFCl-CF_2Cl$ identified by the mass spectrometry.

What we claim is:

1. A process for the preparation of fluorohalogenated ethers having the formula:

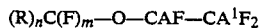

wherein A and A', alike or different from each other, are chlorine or bromine, R is an alkyl or polyether radical containing from 1 to 20 carbon atoms, wholly halogenated with bromine, chlorine and/or fluorine, n is an integer from 1 to 2, m is an integer equal to 3−n, said process consisting in reacting in liquid phase a fluoroxycompound $(R)_nC(F)_m-OF$ with an olefin $CAF=CA'F$, at temperature between −150° and 0° C., characterized in that the fluoroxycompound is continuously fed into the reaction phase in the form of a solution having a concentration less than 50% by weight in an inert solvent, the olefin being fed in the liquid state, optionally in an inert solvent, all at the beginning into the reactor or continuously, in such a manner to have always an excess of the olefin in the reaction phase.

2. Process according to claim 1, wherein a chlorofluorocarbon or a perfluorocarbon or a perfluoroether or a perfluoropolyether is used as inert solvent.

3. Process according to claim 1, carried out at a temperature comprised between −40° C. and −100° C.

* * * * *